United States Patent
Tavares et al.

(10) Patent No.: US 10,464,883 B2
(45) Date of Patent: Nov. 5, 2019

(54) COMPOUNDS AND METHODS FOR THE TREATMENT OF NEURODEGENERATIVE DISEASES

(71) Applicant: Resilio Therapeutics, LLC, Durham, NC (US)

(72) Inventors: Francis Xavier Tavares, Durham, NC (US); Michael Peter Vitek, Efland, NC (US)

(73) Assignee: Resilio Therapeutics, LLC, Durham, NC (US)

( * ) Notice: Subject to any disclaimer, the term of this patent is extended or adjusted under 35 U.S.C. 154(b) by 59 days.

(21) Appl. No.: 15/565,802

(22) PCT Filed: Apr. 11, 2016

(86) PCT No.: PCT/US2016/026951
§ 371 (c)(1),
(2) Date: Feb. 8, 2018

(87) PCT Pub. No.: WO2016/168118
PCT Pub. Date: Oct. 20, 2016

(65) Prior Publication Data
US 2018/0118661 A1 May 3, 2018

Related U.S. Application Data

(60) Provisional application No. 62/147,154, filed on Apr. 15, 2015.

(51) Int. Cl.
| | |
|---|---|
| *C07C 229/46* | (2006.01) |
| *A61K 31/195* | (2006.01) |
| *A61K 31/22* | (2006.01) |
| *C07C 229/26* | (2006.01) |
| *C07D 317/40* | (2006.01) |
| *C07D 211/86* | (2006.01) |
| *C07D 211/90* | (2006.01) |
| *C07C 271/22* | (2006.01) |
| *C07C 275/16* | (2006.01) |
| *C07C 235/34* | (2006.01) |
| *C07C 235/78* | (2006.01) |
| *C07C 251/24* | (2006.01) |
| *A61K 45/06* | (2006.01) |
| *A61P 25/28* | (2006.01) |
| *A61P 25/00* | (2006.01) |
| *A61P 35/00* | (2006.01) |
| *A61K 31/223* | (2006.01) |
| *A61K 31/27* | (2006.01) |
| *A61K 31/357* | (2006.01) |
| *A61K 31/395* | (2006.01) |
| *A61K 31/421* | (2006.01) |
| *A61K 31/4422* | (2006.01) |

(Continued)

(52) U.S. Cl.
CPC ......... *C07C 229/46* (2013.01); *A61K 31/195* (2013.01); *A61K 31/22* (2013.01); *A61K 31/223* (2013.01); *A61K 31/27* (2013.01); *A61K 31/357* (2013.01); *A61K 31/395* (2013.01); *A61K 31/421* (2013.01); *A61K 31/4422* (2013.01); *A61K 31/549* (2013.01); *A61K 31/661* (2013.01); *A61K 31/6615* (2013.01); *A61K 45/06* (2013.01); *A61P 25/00* (2018.01); *A61P 25/28* (2018.01); *A61P 35/00* (2018.01); *C07C 229/26* (2013.01); *C07C 235/34* (2013.01); *C07C 235/78* (2013.01); *C07C 251/24* (2013.01); *C07C 271/16* (2013.01); *C07C 271/22* (2013.01); *C07C 275/16* (2013.01); *C07C 381/00* (2013.01); *C07D 211/86* (2013.01); *C07D 211/90* (2013.01); *C07D 263/44* (2013.01); *C07D 269/00* (2013.01); *C07D 285/34* (2013.01); *C07D 317/36* (2013.01); *C07D 317/40* (2013.01); *C07F 9/06* (2013.01); *C07F 9/09* (2013.01); *C07C 2602/08* (2017.05)

(58) Field of Classification Search
CPC .................................................. C07C 229/46
USPC ....................................................... 514/223.8
See application file for complete search history.

(56) References Cited

U.S. PATENT DOCUMENTS

| | | | | |
|---|---|---|---|---|
| 7,273,888 B2 * | 9/2007 | Ramesh | ................. | A61K 31/00 514/564 |
| 2010/0120727 A1 | 5/2010 | Xu et al. | | |

FOREIGN PATENT DOCUMENTS

WO      WO-2016168118 A1      10/2016

OTHER PUBLICATIONS

"International Application Serial No. PCT/US2016/026951, International Search Report dated Sep. 9, 2016", 4 pgs.

(Continued)

*Primary Examiner* — Taofiq A Solola (74) *Attorney, Agent, or Firm* — Schwegman Lundberg & Woessner, P.A.

(57) ABSTRACT

Novel compounds of formula (II) are disclosed. Compounds of formula (II) comprise ornithine derivatives or compounds that may metabolize to ornithine. Also disclosed are methods for the treatment of neurodegenerative diseases such as Alzheimer's Disease using compounds of formula (II).

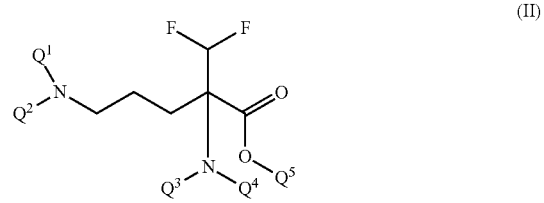

11 Claims, 3 Drawing Sheets

(51) Int. Cl.
*A61K 31/549* (2006.01)
*A61K 31/661* (2006.01)
*A61K 31/6615* (2006.01)
*C07C 271/16* (2006.01)
*C07C 381/00* (2006.01)
*C07D 263/44* (2006.01)
*C07D 269/00* (2006.01)
*C07D 285/34* (2006.01)
*C07D 317/36* (2006.01)
*C07F 9/06* (2006.01)
*C07F 9/09* (2006.01)

(56) References Cited

OTHER PUBLICATIONS

"International Application Serial No. PCT/US2016/026951, Invitation to Pay Add'l Fees and Partial Search Rpt dated Jun. 7, 2017", 2 pgs.

"International Application Serial No. PCT/US2016/026951, Written Opinion dated Sep. 9, 2019", 9 pgs.

"SID 245060932", [Online] retrieved from the internet: <https://pubchem.ncbi.nlm.nih.gov/substance/245060932#sectio>, (Mar. 17, 2015).

Jansson, et al., "Enantioselective and Nonlinear Intestinal Absorption of Eflornithine in the Rat", Antimicrobial Agents and Chemotherapy, vol. 52, [Online] retrieved from the internet: <http://aac.asm.org/content/52/8/2842.full.pdf>, (Jun. 2, 2008).

Loiseau, et al., "Studies on Lipidomimetic Derivatives of alpha-Difluoromethylornithine (dfmo) to enhance the bioavailability in a trypanosoma b. brucei murine trypanosomiasis model. Parasite", [Online] retrieved from the internet: <http://www.parasite-journal.org/articles/parasite/pdf/1998/03/parasite1998053p239.pdf>, (1998), 239-246.

"International Application Serial No. PCT/US2016/026951, International Preliminary Report on Patentability dated Oct. 26, 2017", 8 pgs.

\* cited by examiner

COMPOUNDS AND METHODS FOR THE TREATMENT OF NEURODEGENERATIVE DISEASES

PRIORITY APPLICATIONS

This application is a U.S. National Stage Filing under 35 U.S.C. 371 from International Application No. PCT/US2016/026951, filed on Apr. 11, 2016, and published as WO2016/168118 on Oct. 20, 2016, which claims the benefit of priority to U.S. Provisional Application No. 62/147,154, filed on Apr. 14, 2015; which applications and publication are incorporated herein by reference in their entirety.

BACKGROUND OF THE INVENTION

Alzheimer's disease is an irreversible, progressive brain disease that slowly destroys memory and thinking skills, and eventually even the ability to carry out the simplest tasks. In most people with Alzheimer's, symptoms first appear after age 60. Estimates vary, but experts suggest that as many as 5.1 million Americans may have Alzheimer's disease.

Alzheimer's disease is the most common cause of dementia among older people. Dementia is the loss of cognitive functioning—thinking, remembering, and reasoning—and behavioral abilities, to such an extent that it interferes with a person's daily life and activities. Dementia ranges in severity from the mildest stage, when it is just beginning to affect a person's functioning, to the most severe stage, when the person must depend completely on others for basic activities of daily living.

Alzheimer's disease is named after Dr. Alois Alzheimer. In 1906, Dr. Alzheimer noticed changes in the brain tissue of a woman who had died of an unusual mental illness. Her symptoms included memory loss, language problems, and unpredictable behavior. After she died, he examined her brain and found many abnormal clumps (now called amyloid plaques) and tangled bundles of fibers (now called neurofibrillary tangles). Plaques and tangles in the brain are two of the main features of Alzheimer's disease. The third is the loss of nerve cells (neurons) and the loss of connections between neurons in the brain.

Although we still don't know how the Alzheimer's disease process begins, it seems likely that damage to the brain starts a decade or more before clinically measurable problems become evident. During the preclinical stage of Alzheimer's disease, people are free of overt symptoms while toxic changes are taking place in the brain. Abnormal deposits of proteins form amyloid plaques and tau tangles throughout the brain, and once-healthy neurons begin to work less efficiently. Over time, neurons lose their ability to function and communicate with each other, and eventually they die.

Before long, the damage spreads to a nearby structure in the brain called the hippocampus, which is essential in forming memories. As more neurons die, affected brain regions begin to shrink. By the final stage of Alzheimer's, damage is widespread, and brain tissue has shrunk significantly.

U.S. Pat. No. 7,273,888 discloses the use of difluoromethylornithine (DFMO) for the treatment of amyotrophic lateral sclerosis (ALS) and mentions that polyamine dysregulation may be the cause of many neurodegenerative conditions with Alzheimer's Disease being mentioned among them.

US Patent Application Publication US 2006/0281817 published Dec. 14, 2006 discloses methods for treating a neurodegenerative disease comprising the administration of an ornithine decarboxylase inhibitor.

SUMMARY OF THE INVENTION

Compounds and methods are provided to treat neurodegenerative diseases in humans. The compounds include novel masked or protected reaction products of DFMO, DEMO prodrugs, and other derivatives, such as metabolites and modified metabolites, of difluoromethylornithine.

DETAILED DESCRIPTION OF THE INVENTION

DFMO has a chiral center and compounds of the invention have at least that single chiral center and may have added chiral centers. DFMO has the following formula (I):

$$H_2N-(CH_2)_3-C\cdot(CHF_2)(NH_2)COOH \text{ alternatively depicted as (Ia)}$$

with the e carbon depicted in Formula (I) being chiral. Thus, the two enantiomers of formula (I) are the following R and S isomers designated (I-R) and (I-S), respectively:

Various compounds which metabolize to, and are thus broadly defined, prodrugs of difluoromethylornithine may be used in the present invention. As set forth by K. M Huttunen in Pharmacological Reviews, Vol. 63, No. 3, at pages 750-771 (2011) which is incorporated by reference for teachings of prodrug structures and rationale, "prodrugs" may be defined as inactive, bioreversible derivatives of active drug molecules that must undergo an enzymatic and/or chemical transformation in vivo to release the active parent drug, which can then elicit its desired pharmacological effect in the body of a patient. Compounds of the invention may be active in their own right, may have metabolites which are active other than DFMO or may act as classical prodrugs as so-defined, or combinations thereof.

Compounds of the present invention are DFMO prodrugs where the cleavage during metabolism results in DFMO and one or more moieties which have essentially no toxicity themselves, and include those of the following formula (II):

wherein one or more of $Q^1$, $Q^2$, $Q^3$, $Q^4$ and $Q^5$ is a moiety which is cleavable in vivo to hydrogen and the remainder are hydrogen. In particular one or more of $Q^1$, $Q^2$, $Q^3$, $Q^4$ and $Q^5$ are organic moieities and in particular are metabolized by an esterase. Such moieties include internal bonds such as between $Q^1$ and $Q^5$, an example of which is depicted below as formula (I-1).

$Q^5$ groups used in the present invention include moieties such as those depicted as $R^5$ in WO94/03435 published 17 Feb. 1994 which result in the molecule being an ester, at least in part.

$Q^1$, $Q^2$, $Q^3$ and $Q^4$ groups include monovalent amino-protecting groups, it also being possible for $Q^1$ with $Q^2$, $Q^3$ with $Q^4$ or $Q^1$ with $Q^2$ and $Q^3$ with $Q^4$ in each case together to form a bivalent protecting group. Also included are $Q^1$ together with $Q^3$ forming a bivalent protecting group. Examples of such amino-protecting moieties are described in EP 0644872 published 19 Mar. 1997 with the groups $X_1$, $X_2$, $X_3$ and $X_4$ therein corresponding to the groups $Q^1$, $Q^2$, $Q^3$ and $Q^4$ herein.

As described above, compounds of formula (II) can have the (R) or (S) absolute configuration, depicted below. Any of the compounds of formula (II) can be made as or resolved into the pure (R) or (S) enantiomers by means known in the art. For example, the compounds of formula (II) can be made from enantiopure starting materials, or resolved as diastereomeric salts. Compounds of formula (II) can also be made as racemic mixtures.

In some embodiments, compounds of formula (II) can be diasteromers due to the presence of chiral centers at one or more of $Q^1$ to $Q^5$.

In more detail, compounds of the present invention may be selected from the group consisting of a) an N-acyloxyalkoxy carbonyl derivative of, b) a (phosphoryloxy)methyl carbamate of, c) a redox based system derivative of, d) a beta-aminoketone based derivative of, e) a Schiff base derivative of, f) an N-Mannich base of, g) an (oxodioxolenyl)methyl carbamate of, h) a trimethyl lock system based derivative of, i) an intramolecular bonded derivative of, j) a tetrahydrothiadiazine-2-thione derivative of, and k) a sulfonamide derivative of difluoromethylornithine or a pharmaceutically acceptable salt thereof.

In more detail, compounds of the invention may be selected from the group consisting of the following formulae (A-1) through (L-1). Compounds having the following formulae (A-1) through (L-1) can, although depicted without absolute stereochemistry, can each be pure (R) or (S) enantiomers as described above. Minor modifications are included as part of this invention such as substitution of an alkyl or halo alkyl of 2 to 10 carbons or an aryl or substituted aryl for the pendant methyl(s) of (C-1)-(C-3), (F-1), (G-2), (H-1)-(H-4) or (J-1) or the substitution of a halogen, alkyl or alkoxy for a hydrogen on an aromatic benzene ring(s) of (D-1), (E-1) or (H-1)-(H-3):

(C-1)

(C-2)

(C-3)

(D-1)

(E-1)

(F-1)

(G-1)

(G-2)

(G-3)

(H-1)

(H-2)

(H-3)

(H-4)

(I-1)

-continued (J-1)

(K-1)

(K-2)

(K-3)

(L-1)

wherein $R_1$ is alkyl of about 1-10 carbons, substituted or unsubstituted, aryl of about 6 to 10 carbons, substituted or unsubstituted, or heteroaryl of about 5 to 9 carbons, substituted or unsubstituted;

$R_2$ and $R2'$ are independently hydrogen, alkyl of about 1-10 carbons, substituted or unsubstituted, aryl of about 6 to 10 carbons, substituted or unsubstituted, or heteroaryl of about 5 to 9 carbons, substituted or unsubstituted;

$R_3$ is hydrogen or (a) $C_1$-$C_5$-alkyl,

(b) $C_2$-$C_5$-alkenyl, (c) $C_2$-$C_5$-alkynyl, (d) $(CH_2)_pNR^{12}R^{13}$, (e) $(CH_2)_sCH(R^7)(CH_2)_sO_2CR^8$, (f)

(g) —$(CH_2)_pCO_2R^{10}$, (h)

or (i) $C_1$-$C_5$ alkyl substituted by one or more F;

R is independently a hydrogen, a cation or alkyl of about 1-10 carbons, substituted or unsubstituted, aryl of about 6 to 10 carbons, substituted or unsubstituted, or heteroaryl of about 5 to 9 carbons, substituted or unsubstituted;

$R_4$ is hydrogen, alkyl of about 1-10 carbons, substituted with one or more F, Cl, or Br atoms, or unsubstituted, aryl of about 6 to 10 carbons, substituted or unsubstituted, or heteroaryl of about 5 to 9 carbons, substituted or unsubstituted;

$R_5$ is alkyl of about 1-10 carbons, substituted with one or more F, Cl, or Br atoms, or unsubstituted, aryl of about 6 to 10 carbons, substituted or unsubstituted, or heteroaryl of about 5 to 9 carbons, substituted or unsubstituted;

$R_6$ is alkyl of about 1-10 carbons, substituted with one or more F, Cl, or Br atoms, or unsubstituted, aryl of about 6 to 10 carbons, substituted or unsubstituted, or heteroaryl of about 5 to 9 carbons, substituted or unsubstituted;

$R^7$ is H or $C_1$-$C_5$-alkyl, unsubstituted or substituted with one or more F, Cl, or Br atoms; $R^8$ is (a) H, (b) $C_1$-$C_5$-alkoxy, (c) $C_1$-$C_5$-alkyl optionally substituted with a group consisting of:
  i) $C_1$-$C_5$-alkoxy,
  ii) aryl, wherein aryl is phenyl or napthyl optionally substituted with one or two substituents selected from the group consisting of halo (F, Cl, Br, I), $C_1$-$C_4$-alkyl, $C_1$-$C_4$-alkoxy, —$NO_2$, —$S(O)_r(C_1$-$C_5$-alkyl), —OH, —$NR^{12}R^{13}$, —$CO_2R^{15}$, and —$C_vF_w$ where v=1 to 3 and w=1 to (2v+1), or
  iii) one or more F;

$R^9$ is (a) $C_1$-$C_5$-alkyl, (b) —$C_vF_w$ where v=1 to 3 and w=1 to (2v+1), or (c) $C_1$-$C_5$-alkyl optionally substituted with a group consisting of:
  i) $C_1$-$C_5$-alkoxy,
  ii) phenyl or phenyl substituted with at least one substituent selected from the group consisting of halo (F, Cl, Br, I), $C_1$-$C_4$-alkyl, $C_1$-$C_4$-alkoxy, —$NO_2$, —$S(O)_r(C_1$-$C_4$-alkyl), —OH, —$NR^{12}R^{13}$, —$CO_2R^{15}$, and —$C_vF_w$ where v=1 to 3 and w=1 to (2v+1), or iii) benzyl or benzyl substituted with at least one substituent selected from the group consisting of halo (F, Cl, Br, I), $C_1$-$C_4$-alkyl, $C_1$-$C_4$-alkoxy, —$NO_2$, —$S(O)_r(C_1$-$C_4$-alkyl), —OH, —$NR^{12}R^{13}$, —$CO_2R^{15}$, and —$C_vF_w$, where v=1 to 3 and w=1 to (2v+1);

$R^{10}$ is
(a) phenyl or phenyl substituted with at least one substituent selected from the group consisting of halo (F, Cl, Br, I) $C_1$-$C_4$-alkyl, $C_1$-$C_4$-alkoxy, —$NO_2$, —$S(O)_r$ ($C_1$-$C_4$-alkyl), —OH, —$NR^{12}R^{13}$, —$CO_2R^{15}$, and —$C_vF_w$ where v=1 to 3 and w=1 to (2v+1), or
(b) benzyl or benzyl substituted with at least one substituent selected from the group consisting of halo (F, Cl, Br, I), $C_1$-$C_4$-alkyl, $C_1$-$C_4$-alkoxy, —$NO_2$, —$S(O)_r$ ($C_1$-$C_4$-alkyl), —OH, —$NR^{12}R^{13}$, —$CO_2R^{15}$, and —$C_vF_w$
where v=1 to 3 and w=1 to (2v+1);
$R^{11}$ is H, $C_1$-$C_5$-alkyl or benzyl;
$R^{12}$ and $R^{13}$ are independently H, $C_1$-$C_5$-alkyl, phenyl or benzyl;
$R^{15}$ is H, $C_1$-$C_5$-alkyl, or $NR^{12}R^{13}$;
p is 1-5;
r is 0-2;
s and s' are 0-5;
t is 0 or 1;
$R_8$ is independently (as in K-3) a value of $R^8$ other than (a) H and (b) $C_1$-$C_5$-alkoxy; and
$R_{10}$ is —SR;
or a pharmaceutically acceptable salt thereof. In addition, all of the optical and geometric isomers thereof are included as part of the invention, for example the R, S, Z, E, racemate and enriched enantiomeric variations thereof.

As used herein, "pharmaceutically acceptable salts" include acid or base addition salts, as appropriate for the basic or acidic compound of the invention, respectively. Acids include mineral and organic acids such as hydrochloric, hydrobromic, acetic, citric and benzoic. Bases include ammonia, amines and other nitrogen containing compounds. A more detailed description of pharmaceutically acceptable salt may be found in U.S. Pat. No. 8,202,882 issued Jun. 19, 2012.

DFMO is known as an irreversible inhibitor of ornithine decarboxylase (ODC), an enzyme that catalyzes the conversion of ornithine to putrescine and catalyzing the first step in polyamine biosynthesis. DFMO may have gastrointestinal and hearing loss side effects. Advantages of the invention may include lessening of toxicity in the gut of the patient and/or in the hearing system/circuits/apparatus at an equal molar dose of DFMO. The compounds of the present invention may be administered in doses ranging from about 1 to 20 mg/kg of body weight of the patient administered from 1 to 4 times per day.

Pharmaceutical formulations can be administered in the form of dosage units which comprise a predetermined amount of active compound per dosage unit. Such a unit can comprise, for example, 0.1 mg to 3 g, preferably 1 mg to 700 mg, particularly 5 mg to 100 mg, of a compound according to the invention, depending on the condition treated, the method of administration and the age, weight and condition of the patient, or pharmaceutical formulations can be administered in the form of dosage units which comprise a predetermined amount of active compound per dosage unit. Particular dosage unit formulations are those which comprise a daily dose or part-dose, as indicated above, or a corresponding fraction thereof of an active compound. Furthermore, pharmaceutical formulations of this type can be prepared using a process which is generally known in the pharmaceutical art.

Pharmaceutical formulations can be adapted for administration via any desired suitable method, for example by oral, rectal, nasal, topical or parenteral methods. Such formulations can be prepared using all processes known in the pharmaceutical art by, for example, combining the active compound with the excipients) or adjuvant(s). Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavor, preservative, dispersant and dye may likewise be present.

Capsules are produced by preparing a powder mixture as described above and filling shaped gelatin shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubilizer, such as, for example, agar-agar, calcium carbonate or sodium carbonate, may likewise be added in order to improve the availability of the medicament after the capsule has been taken.

In addition, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets.

A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve, As an alternative to granulation, the powder mixture can be run through a tableting machine, giving lumps of non-uniform shape, which are broken up to form granules. The granules can be lubricated by addition of stearic acid, a stearate salt, talc or mineral oil in order to prevent sticking to the tablet casting molds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units. Oral liquids, such as, for example, solution, syrups and elixirs, can be prepared in the form of dosage units so that a given quantity comprises a pre-specified amount of the compound.

The methods of treatment for compounds of the invention include the methods of prevention, treatment to slow the progress and treatment to reverse the progress of ALS. Neurodegenerative disease as used herein includes, for example, amyotrophic lateral sclerosis (or ALS), Parkinson's disease, multiple sclerosis, and expanded polyglutamine repeat diseases. Expanded polyglutamine repeat diseases (or "polyglutamine repeat diseases) with which the present invention is concerned include, but are not limited to, Huntington's disease, dentatorubral pallidoluysian atrophy, spinobulbar muscular atrophy, and spinocerebellar ataxia types 1, 2, 3, 6 and 7. See, e.g., U.S. Pat. No. 6,632,616 to Burke et al.

The compounds and their pharmaceutical compositions can be used to treat or prevent cognitive deficits and dysfunctions, age-related and otherwise. Among the disorders, diseases, and conditions that the compounds and pharmaceutical compositions of the present invention can be used to treat or prevent are: age-associated memory impairment (AAMI), mild cognitive impairment (MCI), age-related cognitive decline (ARCD), pre-senile dementia, early onset Alzheimer's disease, senile dementia, dementia of the Alzheimer's type, Alzheimer's disease, cognitive impairment no dementia (CIND), Lewy body dementia, HIV-dementia, AIDS dementia complex, and vascular dementia.

Cognitive performance may be assessed with a validated cognitive scale, such as, for example, the cognitive subscale of the Alzheimer's Disease Assessment Scale (ADAS-cog). One measure of the effectiveness of the compounds of the present invention in improving cognition may include measuring a patient's degree of change according to such a scale.

The above conditions and disorders are discussed in further detail, for example, in the American Psychiatric Association: Diagnostic and Statistical Manual of Mental Disorders, Fifth Edition, Text Revision, Washington, D.C., American Psychiatric Association, 2013. This Manual may also be referred to for greater detail on symptoms and diagnostic features.

Combination therapy may be utilized for patients with the compounds and methods of the invention. For example, combinations may be provided with donepezil (Aricept), galantamine (Razadyne), memantine (Namenda), rivastigmine (Exelon), tacrine (Cognex), a BACE inhibitor, (Chiesi Pharmaceuticals), solanezumab or bapineuzumab.

Since DMFO irreversibly inhibits ornithine decarboxylase, which is the first rate-limiting enzyme in polyamine synthesis, DMFO has been shown to have antiproliferative effects in human cancers.

For example, treatment of cancer using DMFO is disclosed in: Simoneau A R, Gerner E W, Nagle R, Ziogas A, Fujikawa-Brooks S, Yerushalmi H, Ahlering T E, Lieberman R, McLaren C E, Anton-Culver H, Meyskens F L Jr., Cancer Epidemiol Biomarkers Prev. 2008 February; 17 (2):292-9. doi: 10.1158/1055-9965. Vlastos A T, West L A, Atkinson E N, Boiko I, Malpica A, Hong W K, Fallen M. Clin Cancer Res. 2005 Jan. 1; 11(1):390-6. Kamat A M, Lamm D L., Urol Clin North Am. 2002 February; 29 (1):157-68. Barranco S C, Townsend C M Jr, Ho B Y, Reumont K J, Koester S K, Ford P J. Invest New Drugs. 1990; 8 Suppl 1:S9-18. Christina M. Laukaitis and Eugene W. Gerner, Best Pract Res Clin Gastroenterol. 2011 August; 25 (4-5): 495-506. Joyce A. O'Shaughnessy1, Laurence M. Demers, Stephen E. Jones, James Arseneau, Pankaj Khandelwal, Timothy George, Robert Gersh, David Mauger and Andrea Manni, Clin Cancer Res November (1999), 5; 3438.

Thus, in some embodiments, the prodrugs of formula (II) are useful for treatment of human cancers. In some embodiments, the treatment comprises administering to a patient in need thereof a composition containing a prodrug of formula (II) as the active agent. In some embodiments, the human cancer is a cancer that affects the digestive tract (e.g. gastric carcinoma or colorectal neoplasia), neuroblastoma, or breast cancer, prostate cancer, cervical cancer, bladder cancer, and glioblastoma. In some embodiments, the treatment of human cancer comprises administering a combination of a prodrug of formula (II) and at least one other anti-cancer agent. The other anti-cancer agent can be an alkylating agent, anti-tumor antibiotic, an anti-metabolite agent, a plant alkaloid or microtubule inhibitor, a DNA linking agent, a biological agent such as an antibody, a bisphosphonate, or a hormone.

In some embodiments, the other anti-cancer agent includes, without limitation, Bendamustine, Busulfan, Carmustine, Chlorambucil, Cyclophosphamide, Dacarbazine, Ifosfamide, Melphalan, Procarbazine, Streptozocin, Temozolomide, and Asparaginase. In some embodiments, the other anti-cancer agent includes, without limitation, Capecitabine, Cytarabine, 5-Fluoro Uracil, Fludarabine, Gemcitabine, Methotrexate, Pemetrexed, and Raltitrexed. In some embodiments, the other anti-cancer agent includes, without limitation, Actinomycin D/Dactinomycin, Bleomycin, Daunorubicin, Doxorubicin, Doxorubicin (pegylated liposomal), Epirubicin, Idarubicin, Mitomycin, and Mitoxantrone. In some embodiments, the other anti-cancer agent includes, without limitation, Etoposide, Docetaxel, Irinotecan, Paclitaxel, Topotecan, Vinblastine, Vincristine, and Vinorelbine.

In some embodiments, the other anti-cancer agent includes, without limitation, Carboplatin, Cisplatin, and Oxaliplatin. In some embodiments, the other anti-cancer agent includes, without limitation, Alemtuzamab, BCG, Bevacizumab, Cetuximab, Denosumab, Erlotinib, Gefitinib, Imatinib, Interferon, Ipilimumab, Lapatinib, Panitumumab, Rituximab, Sunitinib, Sorafenib, Temsirolimus, and Trastuzumab. In some embodiments, the other anti-cancer agent includes, without limitation, Clodronate, Ibandronic acid, Pamidronate, Zolendronic acid. In some embodiments, the other anti-cancer agent includes, without limitation, Anastrozole, Abiraterone, Amifostine, Bexarotene, Bicalutamide, Buserelin, Cyproterone, Degarelix, Exemestane, Flutamide, Folinic acid, Fulvestrant, Goserelin, Lanreotide, Lenalidomide, Letrozole, Leuprorelin, Medroxyprogesterone, Megestrol, Mesna, Octreotide, Stilboestrol, Tamoxifen, Thalidomide, and Triptorelin.

When the prodrug of formula (II) is co-administered with another anti-cancer agent, the administration of the two agents can take place simultaneously (co-administered), or sequentially in any order.

Synthesis of compounds of the invention may be carried out in a manner similar to that of making prodrugs from parent acid or base compounds. Since the DFMO parent compound has both acidic and basic moieties, a wide variety of synthesis approaches can be employed including the step of protecting the acid and/or base moieties, esterification of a pendant carboxylic acid, reaction of a primary amine to create a secondary or even tertiary amine, deprotection, salt formation from a parent acid and salt formation from a parent base. The compounds and intermediates disclosed herein can be prepared by synthetic methods known in the art, including those disclosed in WO 2009/094569.

All patents and patent publications cited herein are hereby incorporated by reference in their entirety.

SYNTHETIC EXAMPLES

Example 1

N-Acyloxyalkoxycarbonyl derivative of DFMO

Prodrug 1

Methylation of DFMO:

To MeOH (50 mL) is added acetyl chloride (7.14 mL, 10 eq) after stirring for 30 minutes, DFMO (0.01 mole) is added. Stirring is continued for 48 hours. After concentration under vacuum, ethyl acetate (500 mL) is added and the contents neutralized (pH=7.2) with saturated $NaHCO_3$. The organic layer is separated, dried and then concentrated under vacuum to afford the methyl ester of DFMO.

Prodrug 1:

To a solution of the DFMO methyl ester (1 mmole) in DMF (5 mL) is added triethyl amine (3 mmole) followed by the addition of chloromethyl chloroformate (2.1 mmole). The contents are stirred for 16 hours to afford the intermediate 1A. To the intermediate 1A, is then added sodium acetate (4 mmole). After stirring for another 20 hours, ethyl acetate (100 mL) and brine (100 mL) is added. The organic layer is separated, dried with magnesium sulfate and then concentrated under vacuum to afford Prodrug 1 (Formula (II) where $Q^1$ and $Q^3$ are $—C(=O)OCH_2OC(=O)CH_3$, $Q^2$ and $Q^4$ are H and $Q^5$ is $—CH_3$).

Example 2

(Oxodioxolenyl)methyl carbamate prodrug

Prodrug 2

Intermediate 2A

To 0.05 g of DFMO in acetonitrile (5 mL) is added Hunigs base (400 µL, 2.3 mmole) followed by the addition of di-tert-butyl dicarbonate (250 µL). The contents are stirred overnight (20 hours). After adding DCM (1 mL) and sonicating, additional Di-tert-butyl dicarbonate is added (100 µL) and then after 15 minutes methanol (1 mL) was added. The mixture is stirred for 3 hours after which thin layer chromatography showed one spot. Concentration under vacuum, add ethyl acetate (15 mL) and ice and acidify to pH=4. Extract, dry ($MgSO_4$) and then concentrate under vacuum and purify using isocratic 10% MeOH in DCM to afford Intermediate 2A (100 mg). ESI (M+Na) (405.2)

Intermediate 2B

To 65 mg (0.00017 mole) of the Intermediate 2A acid in THF/MeOH (9:1) (1 mL) cooled to 0° C. is added TMS diazomethane (170 µL, 2 eq). The mixture is warmed to RT (room temperature) and then stirred for an hour. Acetic acid (200 µL) is added and stirring continued for another 10 minutes to destroy excess TMS diazomethane. Add water and ethyl acetate, extract, concentrate under vacuum to afford the methyl ester Intermediate 2B. ESI (Ma+Na) 419.2

Intermediate 2C

To 0.050 g (0.126 mmole) of Intermediate 2B in THF (0.5 mL) cooled to zero degrees was added NaH (23.2 mg, 4 eq) of NaH. Stir for 15 minutes and then add 4-(bromomethyl)-5-methyl-1,3-dioxol-2-one (48.4 µL). Warm to RT and stir for 2 hours. Add ethyl acetate (10 mL) and water (2 mL), extract, dry and then concentrate the organic layer to afford Intermediate 2C.

Prodrug 2

To 0.1 mmole of Intermediate 2C in THF (2 mL) is added 4N HCl/dioxane (1 mL) stir for 8 hours, add ethyl acetate (10 mL) and neutralize to pH=7.2 with saturated NaHCO$_3$. Separate organic layer, dry with magnesium sulfate and then concentrate under vacuum to afford the Prodrug 2 (Formula (II) where $Q^1$ and $Q^3$ are —CH$_2$-5-methyl-1,3-dioxol-2-one, $Q^2$ and $Q^4$ are H and $Q^5$ is —CH$_3$).

Example 3

Prodrug 3

To 0.1 mmole of the methyl ester of DFMO in DCM (10 mL) cooled to 0° C. is added a 20% solution of phosgene in toluene (0.21 mmole) in the presence of triethylamine (3 eq). After stirring for 24 hours to form the intermediate 3A, 4-(hydroxymethyl)-5-methyl-1,3-dioxol-2-one (0.5 mmole) is then added. Stirring is continued for 24 hours. To the reaction is then added water (5 mL) and then 1 N HCl (5 mL). The organic layer is then separated, dried with sodium sulfate and then concentrated under vacuum to afford Prodrug 3 (Formula (II) where $Q^1$ and $Q^3$ are —C(=O)OCH$_2$-5-methyl-1,3-dioxol-2-one, $Q^2$ and $Q^4$ are H and $Q^5$ is —CH$_3$).

Example 4

In a manner similar to Example 2 with appropriate protection and deprotection reactions, a compound of the invention of Formula (II) wherein $Q^1$, $Q^2$ and $Q^3$ are H, $Q^4$ is —C(=O)OCH$_2$OC(=O)CH$_3$ and $Q^5$ is —CH$_3$ is obtained.

Example 5

Saponification of the product Prodrug 1 of Example 1 results in a compound of the invention of Formula (II) where $Q^1$ and $Q^3$ are —C(=O)OCH$_2$OC(=O)CH$_3$, $Q^2$ and $Q^4$ are H and $Q^5$ is H.

Example 6

In a manner similar to Example 1 with appropriate protection and deprotection reactions, a compound of the invention of Formula (II) wherein $Q^1$, $Q^2$ and $Q^3$ are H, $Q^4$ is —CH$_2$-5-methyl-1,3-dioxol-2-one and $Q^5$ is —CH$_3$ is obtained.

Example 7

Saponification of the product Prodrug 2 of Example 2 results in a compound of the invention of Formula (II) where $Q^1$ and $Q^3$ are —CH$_2$-5-methyl-1,3-dioxol-2-one, $Q^2$ and $Q^4$ are H and $Q^5$ is H.

Compound 1 is synthesized as shown in scheme I, esterification with ethanol in presence of acid afforded the ethyl ester which is then treated with the NHS-acyloxyalkylcarbonate to provide the ethyl ester of 1-(acyloxy) alkyl carbamate prodrug.

17

-continued

Compounds 2-5 are synthesized according to Scheme II. Chloroalkyl chloroformate is treated with the sodium salt of thimethyl to afford the thioester. The chloro group is displaced with various acids in the presence of Hunig's base to afford the acyloxyalkyl derivative of the thioester, treatment of which with NHS in the presence of an oxidizing agent such as peracetic acid afforded the NHS-acyloxyalkylcarbonate. The NHS-acyloxyalkylcarbonates were treated with DFMO in methy tert-butyl ester/water to afford the desired prodrugs.

18

-continued

Compounds 6-8 are synthesized according to Scheme III. Acyl chloride is treated with acetaldehyde in the presence of catalytic zinc chloride to afford the 1-chloralkyl carboxylic esters (A) which are treated with the di-Boc derivative of DFMO to afford the ester. Removal of the Boc group afforded the di amine HCl salt of DFMO prodrug. Treatment of the di HCl salt in presence of a base with NHS-acyloxy-alkylcarbonate afforded the acyloxyalkyl carbamates.

Experimentals

Ethyl 2-amino-2-(difluoromethyl)-5-[1-(2-methyl-propanoyloxy)ethoxycarbonylamino]pentanoate (1)

Step 1: ethyl 2,5-diamino-2-(difluoromethyl)pentanoate 2,5-diamino-2-(difluoromethyl)pentanoic acid (DFMO) 2.0 g (0.011 mole) is suspended in absolute ethanol (30 mL) and then 4N HCl (10 mL) are added. The contents are stirred for 24 hrs and then concentrated under vacuum to afford the ester as a di HCl salt. 1H NMR (599 MHz, DMSO-$d_6$) d ppm 1.17-1.31 (m, 3H) 1.54 (br. s., 1H) 1.74 (br. s., 2H) 1.86-2.02 (m, 1H) 2.76 (br. s., 2H) 4.25 (m, 2H) 6.35 (br. s., 1H), 7.79 (br s 2H). LCMS ESI (M+H) 211.1

Step 2: 1-[(4-amino-5,5-difluoro-4-methyl-pentyl) carbamoyloxy]ethyl 2-methylpropanoate (1)

To ethyl 2,5-diamino-2-(difluoromethyl)pentanoate in methyl tert-butyl ether/water (3:1) is added 1-(2,5-dioxopyrrolidin-1-yl)oxycarbonyloxyethyl 2-methylpropanoate (I) (1 eq) and then contents stirred at room temperature for 24 hrs. Silica gel column chromatography eluting with hexane/ ethyl acetate (0-50%) afforded the desired product (1). 1H NMR (599 MHz, CHLOROFORM-d) d ppm 1.14 (d, J=7.03 Hz, 6H) 1.26-1.31 (m, 3H) 1.43 (d, J=5.27 Hz, 3H) 1.51-1.93 (m, 4H) 2.47-2.56 (m, 1H) 3.18 (m, 2H) 4.16-4.30 (m, 2H) 4.94 (brs, 1H) 5.87 (t, J=54 Hz, 1H) 6.77 (d, J=4.98 Hz, 1H). LCMS ESI (M+H) 369.2

NHS Intermediates

1-(2,5-dioxopyrrolidin-1-yl)oxycarbonyloxyethyl 2-methylpropanoate (I)

(I)

Intermediate (I) is synthesized using literature procedures: 1H NMR (599 MHz, CHLOROFORM-d) d ppm 1.11-1.23 (m, 6H) 1.57-1.65 (m, 3H) 2.58 (m, 1H) 2.77-2.90 (s, 4H) 6.83 (m, 1H).

[1-(2,5-dioxopyrrolidin-1-yl)oxycarbonyloxy-2-methyl-propyl] 2-methylpropanoate (II)

(II)

Intermediate (II) is synthesized using literature procedures: 1H NMR (500 MHz, CHLOROFORM-d) d ppm 0.99-1.06 (m, 6H) 1.14-1.22 (m, 6H) 2.15 (m, 1H) 2.55-2.66 (m, 1H) 2.83 (s, 4H) 6.59 (d, J=4.89 Hz, 1H)

1-(2,5-dioxopyrrolidin-1-yl)oxycarbonyloxyethyl 2,2-dimethylpropanoate (III)

(III)

Intermediate (III) is synthesized using literature procedures: 1H NMR (500 MHz, CHLOROFORM-d) d ppm 1.18-1.23 (s, 9H) 1.60 (d, J=5.38 Hz, 3H) 2.83 (s, 4H) 6.82 (q, J=5.38 Hz, 1H)

[1-(2,5-dioxopyrrolidin-1-yl)oxycarbonyloxy-2-methyl-propyl] 2,2-dimethylpropanoate (IV)

(IV)

Intermediate (IV) is synthesized using literature procedures: 1H NMR (599 MHz, CHLOROFORM-d) d ppm 0.98-1.06 (m, 6H) 1.20-1.25 (s, 9H) 2.08-2.24 (m, 1H) 2.82 (s, 4H) 6.58 (d, J=4.98 Hz, 1H)

2-amino-2-(difluoromethyl)-5-[1-(2-methylpropanoyloxy)ethoxycarbonylamino]pentanoic acid (2)

To a solution of 2,5-diamino-2-(difluoromethyl)pentanoic acid (0.207 mg, 0.948 mmole) in methyl tert-butyl ether/water (3:1, 2.6 mL) is added triethyl amine (0.275 mL), followed by the addition of intermediate (I) (0.259 mg, 1 eq). After stirring for 16 hrs, the contents were evaporated under vacuum. Acidification of the residue with TFA followed by reverse phase HPLC using water/AcCN as the mobile phase afforded (2) as a white solid. 1H NMR (500 MHz, DMSO-d$_6$) d ppm 1.04 (m, 6H) 1.24-1.33 (m, 1H) 1.34-1.41 (m, 3H) 1.41-1.62 (m, 3H) 1.62-1.81 (m, 1H) 2.78-3.02 (m, 1H) 5.98-6.35 (t, J=54 Hz, 1H) 6.50-6.66 (m, 1H) 7.44 (t, J=5.62 Hz, 1H) 7.77 (br. s., 2H). LCMS ESI (M+H) 341.1

2-amino-2-(difluoromethyl)-5-[[2-methyl-1-(2-methylpropanoyloxy)propoxy]carbonylamino]pentanoic acid (3)

(3) is prepared using a similar experimental procedure as for (2). 1H NMR (500 MHz, DMSO-d$_6$) d ppm 0.87 (m, 6H)

0.97-1.10 (m, 6H) 1.30 (m, 1H) 1.40-1.60 (m, 2H) 1.60-1.78 (m, 1H) 1.81-2.01 (m, 1H) 2.56-3.00 (m, 3H) 6.01-6.34 (t, J=54 Hz, 1H) 6.42-6.67 (m, 1H) 7.42 (d, J=5.87 Hz, 1H) 7.77 (br. s., 2H). LCMS ESI (M+H) 369.1

2-amino-2-(difluoromethyl)-5-[(1-(2,2-dimethylpropanoyloxy)ethoxycarbonylamino]pentanoic acid (4)

(4) is prepared using a similar experimental procedure as (2). 1H NMR (500 MHz, DMSO-d$_6$) d ppm 1.08 (s, 9H) 1.29-1.38 (m, 5H) 1.40-1.61 (m, 2H) 2.77-3.01 (m, 2H) 5.96-6.34 (t, J=54 Hz, 1H) 6.60 (q, J=5.38 Hz, 1H) 7.44 (br. s., 1H) 7.67 (br. s., 2H). LCMS ESI (M+H) 355.1

2-amino-2-(difluoromethyl)-5-[[1-(2,2-dimethylpropanoyloxy)-2-methyl-propoxy]carbonylamino]pentanoic acid (5)

(5) is prepared using a similar experimental procedure as (2). 1H NMR (599 MHz, DMSO-d$_6$) d ppm 0.88 (d, J=6.59 Hz, 6H) 1.02-1.16 (s, 9H) 1.32 (br. s., 1H) 1.50 (br. s., 2H) 1.64-1.78 (m, 1H) 1.84-2.04 (m, 1H) 2.79-3.00 (m, 2H) 5.97-6.28 (t, J=54 Hz, 1H) 6.34-6.46 (m, 1H) 7.34 (br. s., 1H) 7.54 (br. s., 2H). LCMS ESI (M+H) 383.2

1-(2-methylpropanoyloxy)ethyl 2-amino-2-(difluoromethyl)-5-[1-(2-methylpropanoyloxy)ethoxycarbonylamino]pentanoate (6)

1-(2-methylpropanoyloxy)ethyl 2,5-bis(tert-butoxycarbonylamino)-2-(difluoromethyl)pentanoate (V)

To 2,5-bis(tert-butoxycarbonylamino)-2-(difluoromethyl)pentanoic acid (0.5 g, 1.31 mmole) in dioxane (6 mL) is added triethyl amine (0.273 mL, 15 eq) followed by the addition of 1-chloroethyl 2-methylpropanoate (0.295 g, 1.5 eq). The contents were heated at 80° C. for 48 hrs. After cooling, the volatiles were evaporated under vacuum and the residue columned on a silica gel column eluting with hexane/ethyl acetate (0-30%) to afford (V) as a colorless oil. 1H NMR (599 MHz, CHLOROFORM-d) d ppm 1.17 (d, J=7.03 Hz, 6H) 1.32-1.50 (m, 18H) 1.53 (d, J=5.56 Hz, 3H) 1.75 (m, 1H) 1.90 (m, 2H) 2.52-2.63 (m, 1H) 3.04-3.22 (m, 2H) 4.63 (br. s., 1H) 5.53 (t, J=54 Hz, 1H) 6.22 (br. s., 1H) 6.87 (d, J=4.98 Hz, 2H). LCMS ESI (M+H) 497.5

1-(2-methylpropanoyloxy)ethyl 2,5-diamino-2-(difluoromethyl)pentanoate (VI)

To (V) (1.0 g, 2.0 mmole) dissolved in dichloromethane (25 mL) is added 4N HCl in dioxane (4 mL). The contents are stirred for 6 hrs at room temperature. Concentration under vacuum afforded the di HCl salt of (VI). 1H NMR (599 MHz, DMSO-d$_6$) d ppm 1.01-1.17 (m, 6H) 1.48 (d, J=5.27 Hz, 3H) 1.76 (m, 1H) 1.89-2.08 (m, 2H) 2.58 (m, 1H) 2.76 (m, 2H) 6.54 (t, J 54 Hz, 1H) 6.76-6.91 (m, 1H) 8.03 (br. s, 3H). LCMS-ESI (M+H) 297.1

1-(2-methylpropanoyloxy)ethyl 2-amino-2-(difluoromethyl)-5-[1-(2-methylpropanoyloxy)ethoxycarbonylamino]pentanoate (6)

To a solution of VI (0.403 mmole) in methyl tert-butyl ether/water (3:1, 2.6 mL) is added triethyl amine (0.226 mL, 4 eq), followed by the addition of intermediate (I) (110 mg, 1eq). After stirring at room temperature for 16 hrs, the contents are evaporated under vacuum to provide a residue that is purified over silica gel using hexane/ethyl acetate (0-50%) as the eluent to afford (6) as a colorless solid. 1H NMR (599 MHz, CHLOROFORM-d) d ppm 0.98-1.37 (m, 12H) 1.36-1.51 (m, 3H) 1.51-1.72 (m, 4H) 1.83-2.15 (m, 2H) 2.28 (m, 1H) 2.42-2.65 (m, 2H) 3.15-3.46 (m, 2H) 4.83 (br. s., 1H) 5.96-6.30 (m, 1H) 6.70-6.82 (m, 1H) 6.83-7.01 (m, 1H). LCMS ESI (M+H) 455.6

1-(2-methylpropanoyloxy)ethyl 2-amino-2-(difluoromethyl)-5-[1-(2,2-dimethylpropanoyloxy)ethoxycarbonylamino]pentanoate (7)

(7) is synthesized using a similar procedure as followed for (6), by treating (VI) with intermediate (III) to afford after purification over silica gel using hexane/ethyl acetate (0-50%) as the eluent (7) as a colorless solid. 1H NMR (599 MHz, CHLOROFORM-d) d ppm 1.02-1.35 (m, 15H) 1.35-1.50 (m, 3H) 1.51-1.72 (m, 4H) 1.83-2.14 (m, 2H) 2.23 (m, 1H) 2.50-2.68 (m, 1H) 3.07-3.39 (m, 2H) 4.82 (br. s., 1H) 5.96-6.17 (m, 1H) 6.67-6.82 (m, 1H) 6.83-7.00 (m, 1H). LCMS ESI (M+H) 469

1-(2-methylpropanoyloxy)ethyl 2-amino-2-(difluoromethyl)-5-[[1-(2,2-dimethylpropanoyloxy)-2-methyl-propoxy]carbonylamino]pentanoate (8)

(8) is synthesized using a similar procedure as followed for (6), by treating (VI) with intermediate (IV) to afford after purification over silica gel using hexane/ethyl acetate (0-50%) as the eluent (8) as a colorless solid. 1H NMR (599 MHz, CHLOROFORM-d) d ppm 0.80-1.04 (m, 6H) 1.08-1.36 (m, 12H) 1.47-1.66 (m, 8H) 1.80-2.14 (m, 2H) 2.22 (m, 1H) 2.49-2.66 (m, 1H) 3.09-3.40 (m, 2H) 4.67-4.90 (br. s, 1H) 6.00-6.32 (m, 1H) 6.45-6.60 (m, 1H) 6.77-6.99 (m, 1H). LCMS (M+H) 497.2

Stability of Prodrugs of DFMO

1. pH Stability

Figure 1:
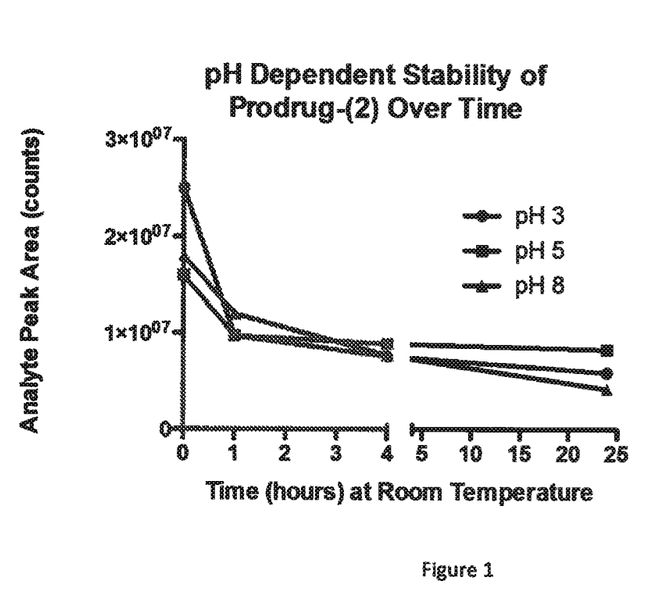
FIG. 1 shows the pH dependent stability of prodrug-(2) over time in aqueous buffer.

The stability of prodrugs of DFMO to different pH conditions over time was assayed. Prodrugs were reconstituted in dimethylsulfoxide (DMSO), diluted into phosphate buffered saline (PBS) of different pH values, incubated for different lengths of time at room temperature, and then analyzed by LC/MS/MS for changes in the levels of each prodrug. As shown in FIG. 1, there was a rapid decrease in the amount of intact, non-degraded (2)-prodrug over the first hour of incubation in PBS buffer that accounts for about 30-35% of the material at pH 5 and 8, and about 60% of the material at pH 3. Following this initial phase, the (2)-prodrug was reasonably stable over the next 24 hours so that less than 20% of the intact prodrug was lost at pH 3 and 5, and about 60% of the intact material was lost at pH 8 over a day. These data show that the intact, non-degraded (2)-prodrug is slowly lost, over time at pH 3, 5 and 8. Similar results were obtained with the other prodrugs tested.

2. Plasma Stability

The stability of the (2)-prodrug in PBS at pH 7.4 in the presence of 10% mouse plasma or 10% human plasma at 25° C. and 37° C. over time was also investigated. Samples were run on an Agilent 1200 HPLC system coupled to an ABI Sciex 4000QTRAP. MRM (341.1/209.2 for 2 and 183.2/120.1 for DFMO) methods were used for quantification of the analytes.

Prodrugs were reconstituted in dimethylsulfoxide (DMSO) at a 10 mM concentration and then diluted into phosphate buffered saline (PBS, pH 7.4) plus 10% human plasma to a final concentration of 20 uM prodrug. Prodrug/human plasma solutions were incubated for different lengths of time at the indicated temperatures, and then analyzed by LC/MS/MS for the accumulation of the mature DFMO product. For LC/MS/MS analysis, each sample was mixed with an equal volume of acetonitrile containing 1 ug/ml of warfarin as an internal standard. The sample/acetonitrile/warfarin solutions were mixed thoroughly and frozen at −80° C. Frozen samples were thawed on ice, centrifuged at 1300×g, the supernatants carefully removed and directly injected 5 ul into the LC/MS/MS. Known amounts of DFMO were run as standards to create a calibration curve for each LC/MS/MS run.

Figure 2:
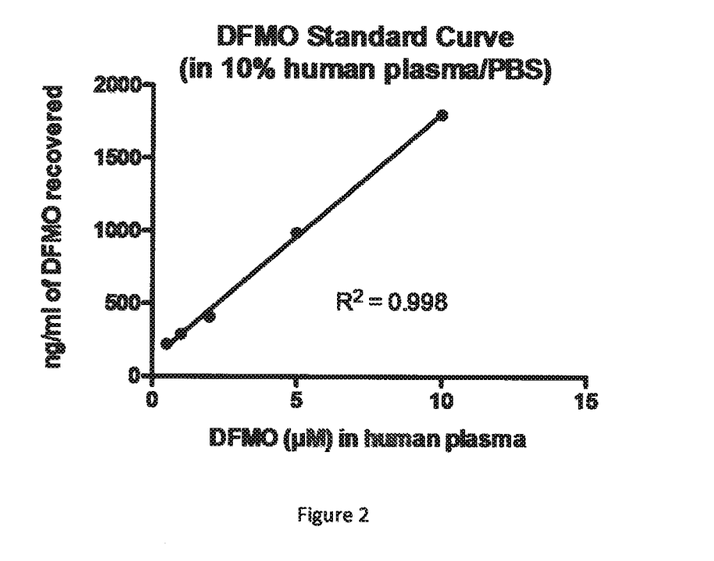
FIG. 2 shows a standard curve for DFMO in 10% human plasma buffered with PBS.
Figure 3:
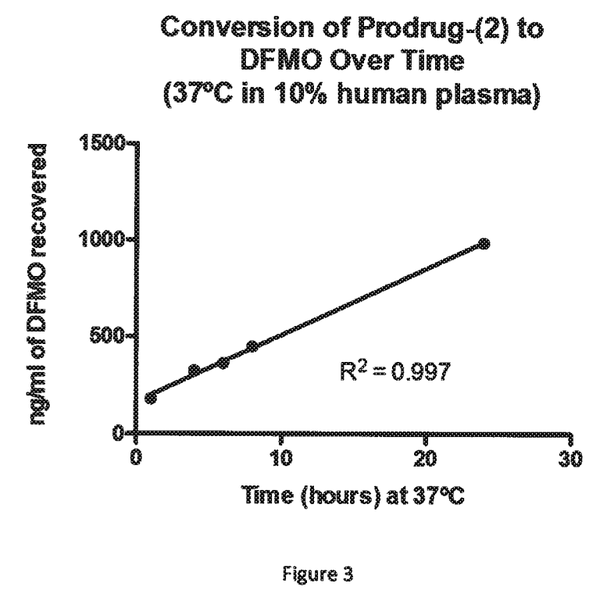
FIG. 3 shows the conversion of prodrug-(2) to DFMO over time in 10% human plasma.

As shown in FIG. 2 the amount of DFMO in plasma was linearly related to the amount of DFMO recovered after extraction and LC/MS/MS analysis ($R^2$=0.998). As shown in FIG. 3, (2)-prodrug was converted to mature DFMO in an linear fashion over time in 10% human plasma at a rate of accumulation of DFMO at 34.09±7.86 ng/hr or in 10% mouse plasma at a rate of accumulation of DFMO at 40.99±1.89 ng/hr. These data suggest that conversion of prodrug into mature DEMO may be slightly faster in mouse compared to human plasma. These data also strongly support that the prodrug is converted to mature DFMO over time in mouse or human plasma.

What is claimed is:

1. A compound selected from the group consisting of:

(A-1)

(A-2)

(A-3)

wherein $R^1$ is alkyl of 1-10 carbons, substituted or unsubstituted, aryl of 6 to 10 carbons, substituted or unsubstituted, or heteroaryl of 5 to 9 carbons, substituted or unsubstituted;

$R^2$ and $R^{2'}$ are independently hydrogen, alkyl of 1-10 carbons, substituted or unsubstituted, aryl of 6 to 10 carbons, substituted or unsubstituted, or heteroaryl of 5 to 9 carbons, substituted or unsubstituted;

$R^3$ is hydrogen or
(a) $C_1$-$C_5$-alkyl,
(b) $C_2$-$C_5$-alkenyl,
(c) $C_2$-$C_5$-alkynyl,
(d) $(CH_2)_p NR^{12}R^{13}$,
(e) $(CH_2)_s CH(R^7)(CH_2)_{s'} O_2 CR^8$, (f)

(g) $-(CH_2)_p CO_2 R^{10}$, (h)

or
(i) $C_1$-$C_5$ alkyl substituted by one or more F;

R is independently a hydrogen, a cation or alkyl of 1-10 carbons, substituted or unsubstituted, aryl of 6 to 10 carbons, substituted or unsubstituted, or heteroaryl of 5 to 9 carbons, substituted or unsubstituted;

$R^7$ is H or $C_1$-$C_4$-alkyl, unsubstituted or substituted by one or more F;

$R^8$ is
(a) H,
(b) C
(c) $C_1$-$C_5$-alkyl optionally substituted with a group consisting of:
i) $C_1$-$C_5$-alkoxy,
ii) aryl, wherein aryl is phenyl or napthyl optionally substituted with one or two substituents selected from the group consisting of halo (F, Cl, Br, I), $C_1$-$C_4$-alkyl, $C_1$-$C_4$-alkoxy, $-NO_2$, $-S(O)_r C_1$-$C_5$-alkyl), $-OH$, $-NR^{12}R^{13}$, $-CO_2 R^{15}$, and $-C_v F_w$ where v=1 to 3 and w=1 to (2v+1), or
iii) one or more F;

$R^9$ is
(a) $C_1$-$C_5$-alkyl,
(b) $-C_v F_w$ where v=1 to 3 and w=1 to (2v+1), or
(c) $C_1$-$C_5$-alkyl optionally substituted with a group consisting of:
i) $C_1$-$C_5$-alkoxy,
ii) phenyl or phenyl substituted with at least one substituent selected from the group consisting of halo (F, Cl, Br, I), $C_1$-$C_4$-alkyl, $C_1$-$C_4$-alkoxy, $-NO_2$, $-S(O)_r C_{1-4}$-alkyl), $-OH$, $-NR^{12}R^{13}$, $-CO_2 R^{15}$, and $-C_v F_w$ where v=1 to 3 and w=1 to (2v+1), or
iii) benzyl or benzyl substituted with at least one substituent selected from the group consisting of halo (F, Cl, Br, I), $C_1$-$C_4$-alkyl, $C_1$-$C_4$-alkoxy, $-NO_2$, $-S(O)_r$ ($C_1$-$C_4$-alkyl), $-OH$, $-NR^{12}R^{13}$, $-CO_2 R^{15}$, and $-C_v F_w$ where v=1 to 3 and w=1 to (2v+1);

$R^{10}$ is
(a) phenyl or phenyl substituted with at least one substituent selected from the group consisting of halo (F, Cl, Br, I), $C_{1-4}$-alkyl, $C_1$-$C_4$-alkoxy, $-NO_2$, $-S(O)_r$ ($C_1$-$C_4$-alkyl), $-OH$, $-NR^{12}R^{13}$, $-CO_2 R^{15}$, and $-C_v F_w$ where v=1 to 3 and w=1 to (2v+1), or
(b) benzyl or benzyl substituted with at least one substituent selected from the group consisting of halo (F, Cl, Br, I), $C_{1-4}$-alkyl, $C_1$-4-alkoxy, $-NO_2$, $-S(O)_r (C_1$-$C_4$-alkyl), $-OH$, $NR^{12}R^{13}$, $-CO_2 R^{15}$, and $-C_v F_w$ where v=1 to 3 and w=1 to (2v+1);

$R^{11}$ is H, $C_1$-$C_5$-alkyl or benzyl;
$R^{12}$ and $R^{13}$ are independently H, $C_1$-$C_5$-alkyl, phenyl or benzyl;
$R^{15}$ is H, $C_1$-$C_5$-alkyl, or $NR^{12}R^{13}$;
p is 1-5;
r is 0-2;
s and s' are 0-5;
t is 0 or 1;
$R_8$ is independently a value of $R^8$ other than (a) H and (b) $C_1$-$C_5$-alkoxy; and
$R_{10}$ is $-SR$;
or a pharmaceutically acceptable salt thereof.

2. The compound of claim 1, or a pharmaceutically acceptable salt thereof which is in the R configuration corresponding to R-ornithine.

3. The compound of claim 1, or a pharmaceutically acceptable salt thereof, which is in the S configuration corresponding to S-ornithine.

4. The compound of claim 1, wherein the compound is a compound of the formula:

(A-1)

or a pharmaceutically acceptable salt thereof.

5. The compound of claim 4, or a pharmaceutically acceptable salt thereof, wherein:
$R^1$ is alkyl of 1-10 carbons; and
$R^2$ and $R^{2'}$ are independently hydrogen or alkyl of 1-10 carbons.

6. The compound of claim 4, or a pharmaceutically acceptable salt thereof, wherein:
$R^3$ is hydrogen or $C_1$-$C_5$-alkyl.

7. The compound of claim 5, or a pharmaceutically acceptable salt thereof, wherein:
$R^3$ is hydrogen or $C_1$-$C_5$-alkyl.

8. The compound of claim 4, or a pharmaceutically acceptable salt thereof, wherein:
$R^1$ is alkyl of 1-4 carbons; and
$R^2$ and $R^{2'}$ are independently hydrogen or alkyl of 1-3 carbons.

9. The compound of claim 7, or a pharmaceutically acceptable salt thereof, wherein:
$R^3$ is hydrogen or $C_1$-$C_5$-alkyl.

10. The compound of claim 8, or a pharmaceutically acceptable salt thereof, wherein:
$R^3$ is hydrogen or $C_1$-$C_5$-alkyl.

11. The compound of claim 4, or a pharmaceutically acceptable salt thereof, wherein the compound is a compound of the formula: